United States Patent [19]

Witt et al.

[11] Patent Number: 5,110,905

[45] Date of Patent: May 5, 1992

[54] **ACTIVATED *BACILLUS THURINGIENSES* DELTA-ENDOTOXIN PRODUCED BY AN ENGINEERED HYBRID GENE**

[75] Inventors: Daniel P. Witt, South Hamilton; Donald A. Colbert, Scituate; Algis Anilionis, Arlington, all of Mass.

[73] Assignee: Repligen Corporation, Cambridge, Mass.

[21] Appl. No.: 559,223

[22] Filed: Jul. 27, 1990

Related U.S. Application Data

[63] Continuation of Ser. No. 745,354, Jun. 14, 1985, abandoned.

[51] Int. Cl.$^5$ .................. C07K 3/00; C12P 21/06; C12P 21/04
[52] U.S. Cl. .................................. 530/350; 435/69.1; 435/71.1
[58] Field of Search ............... 530/324, 350; 435/69.1, 435/69.7, 71.1, 172.1, 252.3; 536/24

[56] References Cited

U.S. PATENT DOCUMENTS 4,652,628  3/1987  Walfield et al. ................... 530/324

OTHER PUBLICATIONS

Lilley Purification of the Insecticidal Toxin in Crystals of *Bacillus thurgingiensis*, The Journ. of Gen. Microb. 118;1-11 1980.

Shibano, Nucleatide Sequence Coding for the insecticidal Fragment of the *Bacillus thuringiensis* Crystal Protein, Gene 34: 243-251, 1985.

Schnepf et al., Delinealion of a Toxin-Encoding Segment of a *Bacillus thuringiensis* Crystal Protein Gene, The Journal of Biol. Chem. 260:6273-6280 1985.

Wong et al., Transcriptional & Translational Start Sites for the *Bacillus thuringiensis* Protein Gene, The Journal of Biol. Chem. 258:1960-1967, 1983.

*Primary Examiner*—Christine Nucker
*Assistant Examiner*—Hazel F. Sidberry
*Attorney, Agent, or Firm*—Gerald D. Sharkin; Richard E. Vila

[57] ABSTRACT

The subject invention is directed to a novel *Bacillus thuringiensis* kurstaki δ-endotoxin prepared by use of a novel hybrid gene. This gene is cloned into a novel plasmid which is transformed into a prokaryotic host. The δ-endotoxin of the subject invention is active against Lepidoptera larvae.

4 Claims, 2 Drawing Sheets

(1) Bam/Pst Digestion (2) Gel Purification of A and B Fragments of pBR322, and A' and B' Fragments of pK15

(3) Ligation of A + A' and B + B' Fragments

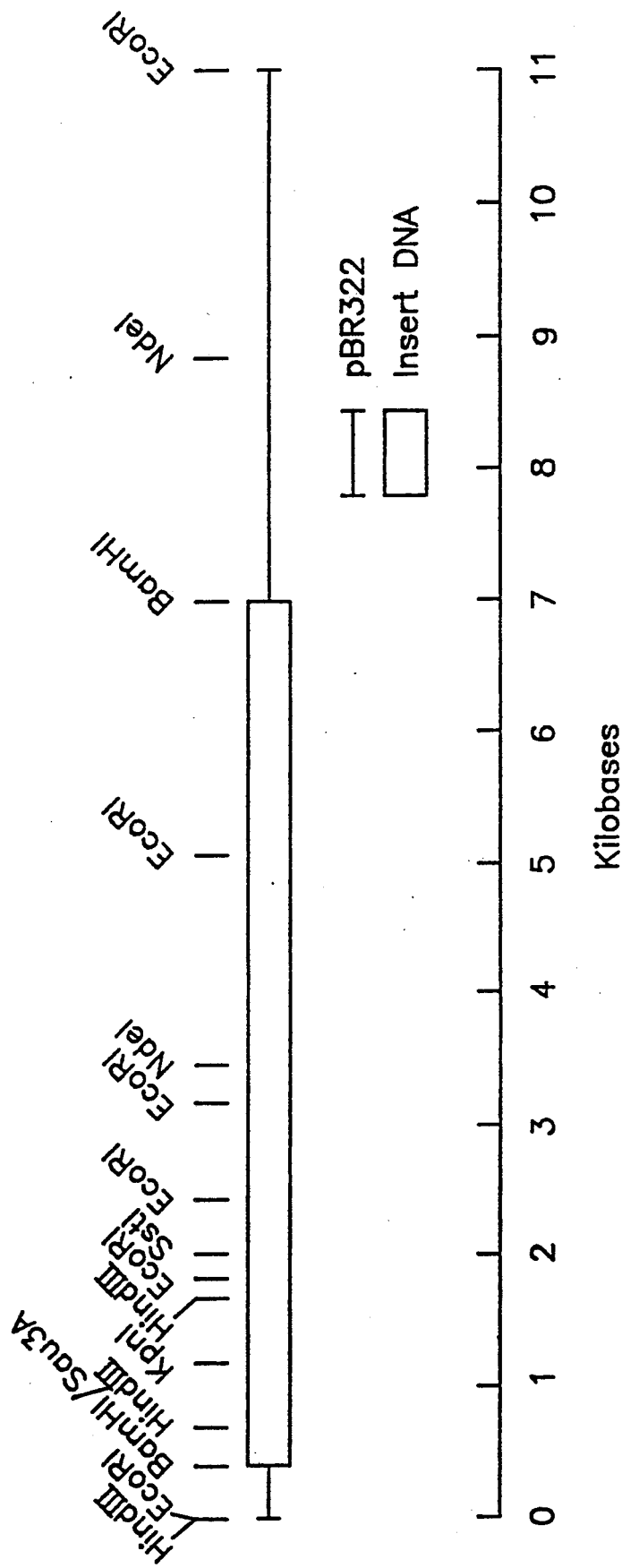

ACTIVATED BACILLUS THURINGIENSES DELTA-ENDOTOXIN PRODUCED BY AN ENGINEERED HYBRID GENE

This application is a continuation of application Ser. No. 06/745,354 filed Jun. 14, 1985 now abandoned.

BACKGROUND OF THE INVENTION

*Bacillus thuringiensis*, a spore-forming bacterium of which there are more than 200 naturally occurring variants, produces a rhombic crystal during sporulation. This crystal is toxic upon ingestion to a wide variety of lepidopteran larvae. Many of these susceptible larvae are economically important crop pests. The toxic factor in the crystal is derived from a protein protoxin of molecular weight 130,000 which has been termed the $\delta$-endotoxin; the protoxin is not in itself toxic but requires proteolytic processing to yield an active toxin (activated $\delta$-endotoxin), and processing normally occurs in the insect gut.

*Bacillus thuringiensis* (*B.t.*) toxin has provided a basis for commercial formulations of insecticide for at least ten years. The active ingredient in these products is dried preparations of sporulated *B.t.* cells. Included in this dried powder is the rhombic crystal and the viable spore which can regenerate to give rise to vegetative *B.t.* cells.

The commercial formulations of *B.t.* have found use in markets ranging from vegetables to forest management. Limitations to the use of this product, however, include:

1. Instability of the toxin gene in the micro-organism results in difficulties in quality control.
2. Problems in application arise, as the toxin is in particulate rather than soluble form.
3. Speed of action is slower than that of chemical pesticides, possibly because of the requisite protoxin to toxin activation step.
4. Manifestation of toxicity requires ingestion of the toxic crystal by a susceptible insect.
5. Commercial preparations contain viable spores.

In spite of these limitations, use of *B.t.* preparations has been increasing, particularly in such areas as forest pest management The reasons for this include:

1. The toxin is highly specific to target insect pests and is inactive against other life forms, including beneficial insects.
2. The active factor is a protein molecule and, as a consequence, is rapidly biodegradable and poses little risk of long term impact on the ecosystem.

In 1981, a gene encoding the protoxin from a commercial strain of *B.t.* was cloned and expressed in *E. coli* by Schnepf and coworkers (Schnepf, H. E. and Whiteley, H. R. [1981] *Proc. Natl. Acad. Sci USA* 78: 2893-2897) A U.S. patent was granted on this construction (U.S. Pat. No. 4,448,885). The recombinant plasmid encodes the entire protoxin molecule and the gene is under the control of its natural promoter. Subsequently, a European patent has been filed by Klier et al on a recombinant protoxin gene from what is presumably a different strain (*B. thuringiensis* 1715) (Klier, A., Rapoport, G., Dedonder, R. [Filing date Apr. 26, 1982] Demande de Brevet Europeen 0 093 062). In neither of these patents is the sequence of the gene or the protein product disclosed It is clear that the toxin genes in both cases are bounded by undefined sequences of DNA.

BRIEF SUMMARY OF THE INVENTION

The subject invention concerns the engineering of a plasmid that encodes preactivated *B.t.* $\delta$-endotoxin. No processing of the gene product is required for activity. This plasmid contains an engineered gene consisting of a fragment of the *B.t.* $\delta$-endotoxin gene encoding a $\sim$70,000d protein which is identical or nearly identical to the activated $\delta$-endotoxin produced by proteolysis of the protoxin molecule. Thus the activated toxin is a direct product of protein synthesis and does not require additional processing. The advantages of this genetic construction are as follows:

1. The gene is more stable than its counterpart in *B.t.* and may be more stable than the relatively undefined fragment of DNA cloned by either Schnepf et al (Schnepf, H. E. and Whiteley, H. R., U.S Pat. No 4,448,885) or Klier et al. (Klier, A., Rapoport, G., Dedonder, R [Filing date Apr. 26, 1982] Demande de Brevet Europeen 0 093 062). The instability of the naturally occurring gene may arise because it lies within a transposon-like structure (Lereclus, D., Ribier, J., Klier, A., Menou, G. and Lecadet, M. M. [1984] *EMBO Journal* 3:2561-2567). Inverted repeat sequences that are characteristic of a transposon have been eliminated from the plasmid of the subject invention.
2. The activated $\delta$-endotoxin produced directly from the hybrid gene is, in essence, a chemical product. The formulation in which it is applied for pest control will contain no viable microorganisms or spores. This constitutes a significant advantage over the commercial preparations presently in use that result in the application of viable spores into the environment.
3. The activated $\delta$-endotoxin produced by the hybrid gene is insoluble but is readily extracted into soluble form in aqueous solutions. This can present advantages for application. Insoluble toxin crystals derived from *B.t.* may present problems with regard to application and coverage. These problems are obviated with a soluble preparation.
4. The theoretical rate of expression is increased at least two-fold over the constructions patented by either Schnepf, et al. (Schnepf, H. E. and Whiteley, H. R., U.S. Pat. No. 4,448,885) or Klier et al. (Klier, A., Rapoport, G., Dedonder, R. [Filing date Apr. 26, 1982] Demande de Brevet Europeen 0 093 062), as the recombinant gene product of the hybrid gene is only half as large as the entire protoxin. The advantages may be greater than this as the C-terminal half of the molecule, which has been eliminated in the construction, may result in a growth/expression limitation in *E. coli*.
5. The specific activity of the activated molecule produced by the hybrid gene is effectively double that of the protoxin, as the half of the molecule that makes no contribution to toxicity has been eliminated. Thus, on a weight basis, the activity of the material is about twice that of the protoxin produced by the recombinant plasmid of either Schnepf et al. (Schnepf, H. E. and Whiteley, H. R., U.S. Pat. No. 4,448,885) or Klier et al. (Klier, A., Rapoport, G., Dedonder, R. [Filing date Apr. 26, 1982] Demande de Brevet Europeen 0 093 062).
6. The protein produced by the hybrid gene is a preactivated toxin and requires no further processing or alteration for full activity. In contrast, the δ-endotoxins derived from the natural source as well as those expressed by the recombinant plasmid of others (Schnepf, H. E. and Whiteley, H. R., U.S. Pat. No. 4,448,885):Klier, A., Rapoport, G., Dedonder, R. [Filing date Apr. 26, 1982] Demande de Brevet Europeen 0 093 062) are inactive molecules and require proteolytic processing for activity (Lecadet, M. M. and Dedonder, R. [1967] *J. Invert. Pathol.* 9:322). Although processing of these protoxins can occur in the insect gut, this preactivation may provide an improvement in speed of kill, an important consideration in the commercial utilization of *B.t.* toxin.

The nucleotide sequence of the engineered gene of the subject invention is shown in CHART A. Also shown in CHART A is the deduced amino acid sequence of the activated *B.t.* δ-endotoxin.

The nucleotide sequence, and deduced amino acid sequence, of the essential *B.t.* δ-endotoxin fragment lying between codons 566 and 608 are shown in CHART B. The codons which are conserved between divergent genes are indicated within the blocked areas. Codons in which substitutions are allowed, while still maintaining the insecticidal property of the expressed protein, are $Asn_{576}$, $Ser_{578}$, $Asn_{579}$, $Gly_{580}$, $Ser_{581}$, $Val_{583}$, $Leu_{586}$, $Ser_{587}$, $His_{589}$, $Val_{590}$, $Asn_{592}$, and $Ala_{607}$. Thus, substitution with any amino acid, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, can be made in at least 12 positions of the sequence while still retaining insecticidal activity of the δ-endotoxin.

DESCRIPTION OF THE DRAWINGS

FIG. 2: Restriction Map of Plasmid pK8-1.

DETAILED DESCRIPTION OF THE INVENTION

A δ-endotoxin gene was cloned from a 72 Md plasmid from *Bacillus thuringiensis* var.kurstaki (*B.t.k.*). Cloning is described in the Examples. The resulting recombinant plasmid, pK15, when transformed into *E. coli* expressed a protein that reacted with antisera directed toward *B.t.k.* endotoxin and was toxic to tobacco budworm (TBW) larvae.

Figure 1:
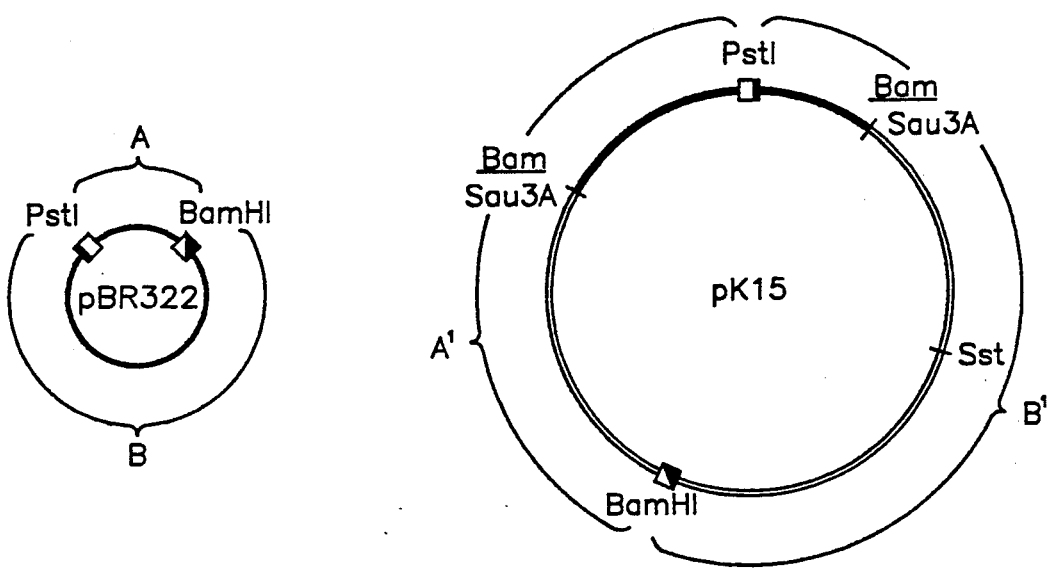
FIG. 1: Construction Scheme Showing the Preparation of Plasmids pK7-3 and pK8-1 from Plasmids pBR322 and pK15.
Figure 1:
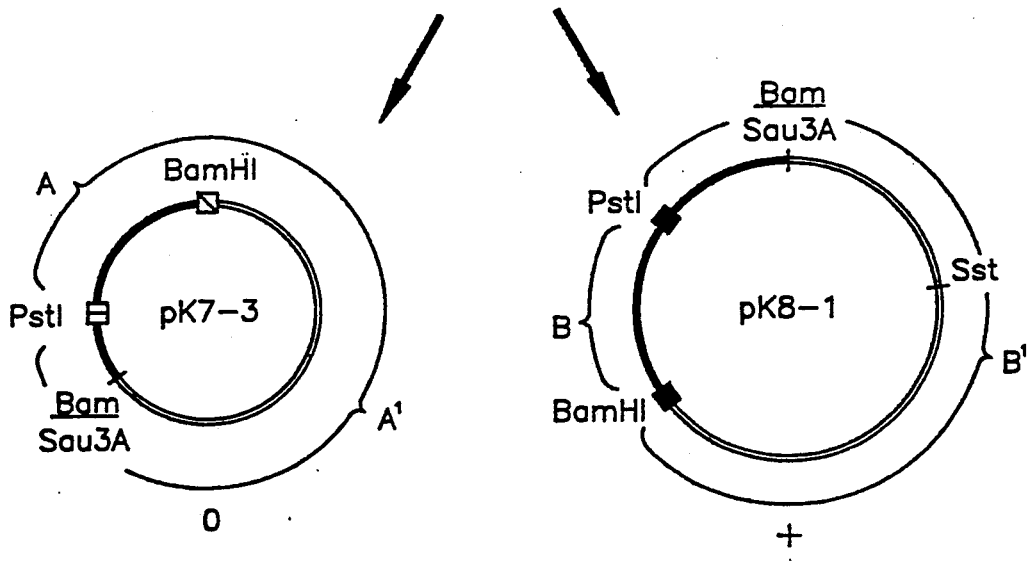

Subcloning of the gene was accomplished by first digesting pK15 with BamHI and PstI restriction endonucleases (double digest to generate two fragments). Recombination of these fragments with similarly digested pBR322 yielded two plasmids. One of these, pK8-1 (FIG. 1), was found to contain the complete δ-endotoxin gene present in pK15.

This insert was sequenced by the technique of Maxam and Gilbert (Maxam, A. M. and Gilbert, W. [1977] *Proc. Natl. Acad. Sci.* 74:560). An open reading frame was identified and the amino acid sequence of the activated δ-endotoxin was determined from subclone pK8-1.

Amino terminal analysis of activated toxic protein from *B.t. kurstaki* crystals was conducted and the sequence was found to be:

Gly Glu X Ile Glu Thr corresponding to the hexapeptide at codons 26–31 of the *B.t.k.* gene:

Gly Glu Arg Ile Glu $Thr^{31}$.

This permitted accurate location of the amino terminus of the processed and activated δ-endotoxin within the protoxin molecule.

The carboxy terminus of the activated toxin molecule was determined by digestion with carboxypeptidase Y and the sequence of the predominant species was found to be Val-Thr. Consideration of the molecular weight of the protein and its predicted amino acid sequence resulted in the assignment of Val-$Thr^{610}$ as the likely C-terminus of the predominant species. The sequence disclosed in CHART A includes two amino acid changes to Lys-His at positiors 609 and 610 of the naturally occurring molecule. The major species present in the bromelan-activated endotoxin is therefore predicted to be 585 amino acids in length and has a calculated molecular weight of 65,406 daltons. The N-terminus lies at codon 26 and the C-terminus of the principal species of the activated molecule at codon 610.

A plasmid, named pΔ649, was constructed in which sequences in the 3' half of the structural gene which encode nontoxic and possibly inhibitory regions were deleted while the region encoding the processed protein described above was retained. To produce this construction, advantage was taken of a KpnI site at codon 722/723 in the *B.t. kurstaki* δ-endotoxin gene. This unique restriction endonuclease site lies 81 codons downstream (i.e., within the protoxin sequences) from the codon that marks the principal end of the protease-activated toxin. The parent plasmid is opened at the KpnI site and digested with Ba131, a double-stranded exonuclease. Religation after a variable period of time gives rise to a series of plasmids containing δ-endotoxin genes with truncations at the 3' end. The shortest member of this series that showed full toxicity toward tobacco budworm larvae was designated pΔ649. This clone expressed a protein of MW 66,000d which reacted with antisera directed toward the *B.t. kurstaki* δ-endotoxin. Nucleotide sequencing of this construction revealed that the δ-endotoxin is terminated at codon 608. Two missense amino acids, lysine and histidine, are followed by a stop codon. An abrupt and dramatic decline in toxicity was found in other constructions which ended upstream from codon 608. The low level of toxicity seen with these truncated gene products was retained by considerably shorter proteins.

These studies have allowed the identification of a sequence at the carboxy-terminus of the activated *B.t.* δ-endotoxin molecule which is essential to the biological activity of the toxin. This sequence is no more than 45 amino acids in length and is shown in CHART B. Amino acid substitutions are allowed at least at twelve codons. These are also shown in CHART B. This sequence is not by itself toxic but is an essential component of the active δ-endotoxin and defines the extreme carboxy-terminus of the functional molecule. Proteins that have lost this sequence or that terminate within it display markedly lowered activity toward lepidopteran larvae.

The essential functional δ-endotoxin lies between codon 26 and codon 608 of the protoxin gene. A sequence at the carboxy terminus of the molecule lying between codons 566 and 608 (CHART B) is essential to the biological activity of the molecule Toxicity is much less sensitive to alterations in amino acids lying at the N-terminus.

Following are examples which illustrate procedures, including the best mode, for practicing the invention.

These examples should not be construed as limiting. All percentages are by weight and all solvent mixture proportions are by volume unless otherwise noted.

EXAMPLE 1

Construction of Recombinant Plasmid pK15.

Preparation of plasmid DNA from *B.t. kurstaki* cells (NRRL B-15974) was initiated by growing cells on L-broth (1 liter) to $A_{600}=0.6$. The cells were pelleted by centrifugation (5 Krpm, 10 min, 4° C.), resuspended in cold TES buffer (30 mM Tris-HCl, pH 8.0, 50 mM EDTA) and repelleted. Lysis was carried out by resuspending the cells in 4 ml lysozyme buffer (30 mM Tris-HCl, pH 8.0, 50 mM NaCl, 25% sucrose), followed by the addition of 0.2 ml 10 mg/ml lysozyme solution, and incubated at 37° C., 30 min. 16 ml of SDS buffer (1.25% SDS, 60 mM EDTA, 10 mM Tris pH 8.0) and 5 ml 5M NaCl were then added and the cells allowed to stand on ice for 3 hr. Following pelleting of cell debris by centrifugation (15 Krpm, 30 min, 4° C.), 5 ml of 50% PEG6000 was added, mixed gently and allowed to stand on ice for 1-3 hr. The resulting precipitate was pelleted by centrifugation (10 Krpm, 10 min, 4° C.), redissolved in 2 ml TES buffer and treated with pancreatic ribonuclease (200 μg/ml, 65° C., 30 min). Ethidium bromide was then added (0.1 ml of 10 mg/ml stock) and the volume adjusted to 4 ml with TE buffer (10 mM Tris-HCl pH 8.0, 1 mM EDTA ). CsCl was then added (7.3 g/8 ml) and the plasmid DNA banded by centrifugation (48-72 hr, 42 Krpm, in Beckman Ti50 rotor). Localization, harvesting, and treatment of the resulting plasmid DNA was carried out using standard procedures Routine yields of plasmid DNA were about 200 μg per liter cells.

*B.t.k.* plasmid DNA was isolated, as described above, and partially digested with Sau3A restriction endonuclease (100 μg/ml DNA, 17 μ/ml Sau3A, 2.5 min, 37° C.). The resulting *B.t.k.* DNA fragments (5 μg) were ligated with T4 ligase. The 130,000 dalton *B.t.k.* δ-endotoxin should be coded for by a DNA fragment 3.5-4.0 kilobases (Kb) in length. To insure a greater chance of cloning the entire protoxin gene, including promoter, ribosome binding site, and termination signal, an enrichment scheme was carried out in order to obtain recombinant plasmids with insert *B.t.k.* DNA of 45 greater size than the predicted gene length.

Restriction endonuclease data reported by Schnepf and Whiteley (Schnepf, H. E. and Whiteley, H. R. [1981] *Proc. Natl. Acad. ScL USA* 78:2893-2897) indicated that SalI does not cut the *B.t.k.* δ-endotoxin gene or its immediately adjacent flanking sequences. Utilizing this information, the ligated *B.t.k.* recombinant plasmids were linearized by SalI digestion and fractionated by preparative agarose gel electrophoresis. Recombinant plasmid DNAs of greater than 10 Kb length (putative insert DNA greater than 6 Kb) were extracted from the gel, circularized with T4 ligase, and used to transform *E. coli* MS371 cells. Of the first 53 Amp$^r$/Tet$^s$ recombinant colonies, 24 were picked for minilysate preparation and restriction enzyme analysis. The size of the insert *B.t.k.* DNA ranged from 3.9 and 14.7 Kb length with a mean insert length of 6.7 Kb. Cell extracts from one recombinant plasmid, designated pK15, were found to react positively with antisera prepared against *B.t.k.* 130,000 protoxin, and were toxic to *Heliothis virescens* larvae in the insect toxicity assay. Since no significant reaction with the antisera or larval toxicity was observed with cell extracts from *E. coli* carrying either pBR322 or recombinant plasmids carrying other *B.t.k.* plasmid DNA inserted, it was concluded that the *B.t.k.* insert DNA of pK15 contains at least a portion of the δ-endotoxin gene.

The isolated DNA was then digested with Sau.3A restriction endonuclease (100 μg/ml DNA, 17 u/ml Sau3A, 2.5 min, 37° C.). The resulting *B.t.k.* DNA fragments (5 μg) were mixed with BamHI digested pBR322 plasmid DNA (1.25 μg) and ligated with T4 ligase. The 130,000 *B.t.k.* δ-endotoxin should be coded for by a DNA fragment 3.5-4.0 kilobases (Kb) in length. In order to insure a greater chance of cloning the entire protoxin gene, including promoter, ribosome binding site, and termination signal, an enrichment scheme was carried out in order to obtain recombinant plasmids with insert *B.t.k.* DNA of greater size than the predicted gene length.

The ligated *B.t.k.* recombinant plasmids were linearized by SalI digestion and fractionated by standard preparative agarose gel electrophoresis. Recombinant plasmid DNAs of greater than 10 Kb length (putative insert DNA greater than 6 Kb) were extracted from the gel, circularized with T4 ligase, and used to transform *E. coli* MS371 cells. Of the first 53 Amp$^r$/Tet$^s$ recombinant colonies, 24 were picked for mini-lysate preparation and restriction enzyme analysis. The size of the insert *B.t.k.* DNA ranged between 3.9 and 14.7 Kb length with a mean insert length of 6.7 Kb Cell extracts from one recombinant plasmid, designated pK15, were found to react positively with antisera prepared against *B.t.k.* 130,000 protoxin, and were toxic to *Heliothis virescens* larvae in an insect toxicity assay Since no significant reaction with the antisera or larval toxicity was observed with cell extracts from *E. coli* carrying either pBR322 or recombinant plasmids carrying other *B.t.k.* plasmid DNA inserted, it was concluded that the *B.t.k.* insert DNA of pK15 contains at least a portion of the δ-endotoxin gene.

EXAMPLE 2

Preparation of Recombinant Plasmids pK7-3 and pK8-1.

Plasmid pK15. prepared as described in Example 1, was digested with BamHi and PstI restriction endonucleases. This double digest yielded two fragments. The fragments were isolated by standard gel electrophoresis. Plasmid pBR322 was similarly digested to yield two fragments that were isolated in a similar manner.

The two fragments from plasmid pK15 were then ligated with the two fragments obtained from digestion of pBR322. The ligation was conducted under standard conditions using T4 ligase. The result of this ligation was two plasmids designated pK7-3 and pK8-1. See FIG. 1 of the drawing. Plasmid pK8-1 was found to contain the complete δ-endotoxin gene present in plasmid pK15.

EXAMPLE 3

Preparation of *B.t.k.* δ-Endotoxin Mutant 649 of Recombinant Plasmid pΔ649.

Mutation 649 can be constructed by opening at the unique KpnI site in the *B.t.k.* gene and bilaterally digesting with Bal31. The digestion with this exonuclease is terminated after ~350 nucleotides are removed upstream from the KpnI site. The necessary incubation time for this reaction will vary with preparations of Ba131 and must be monitored by agarose gel electrophoresis of religated and HindIII digested samples taken at various time points The HindIII fragment of pK8-1 is 1050 bp while that of pΔ649 is 285 bp.

Sequencing by the technique of Maxam and Gilbert (Maxam, A. M. and Gilbert, W [1977] *Proc. Natl. Acad. Sci.* 74:560) revealed that pΔ649 terminated at Glu608 of the δ-endotoxin sequence and was fused with an unrelated dipeptide, Lys-His. These two amino acids arise as a result of a frame-shift and a missense readthrough and are followed in the construction by a termination codon The full length gene product is thus 610 amino acids long, 608 amino acids of which are derived from the δ-endotoxin sequences. The gene product is fully active in a bioassay utilizing tobacco budworm larvae. Gene products expressed by shorter constructions are markedly decreased in activity.

Plasmids pK8-1 and pΔ649 have been transformed into *E. coli* hosts by standard procedures. A subculture of these hosts containing these plasmids have been deposited in the permanent collection of the Northern Regional Research Laboratory, U.S. Department of Agriculture, Peoria, Ill., USA. The cultures were assigned the following accession numbers by the repository:

*E. coli* MS371(pK8-1)—NRRL B-15967. Deposited on Apr. 24, 1985.

*E. coli* SG4044(pΔ649)—NRRLB-15968. Deposited on Apr. 24, 1985.

*E. coli* SG4044—NRRL B-15969. Deposited on Apr. 24, 1985.

*E. coli* MS371—NRRL B-15129. Deposited on Aug. 18, 1982.

*B. thuringiensis* kurstaki HD1R—NRRL B-15974. Deposited on Jun. 6, 1985.

These deposits are available to the public upon the grant of a patent disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

Plasmid pBR322 is a well-known and available plasmid. It is maintained in the *E. coli* host ATCC 37017. Purified pBR322 DNA can be obtained as described in Bolivar, F., Rodriquez, R. L., Greene, P. J., Betlach, M. C., Heyneker, H. L., Boyer, H. W., Crosa, J. H., and Falkow, S. (1977) Gene 2:95-113; and Sutcliffe, J. G. (1978) Nucleic Acids Res. 5: 2721-2728.

EXAMPLE 4

Preparation of Recombinant Plasmid pKΔH

Plasmid pKΔH can be made by digesting plasmid pK8-1 with HindIII endonuclease and religating by standard procedures. This results in the deletion of a 1750 bp fragment that stretches between the righthand HindIII site shown in the map of plasmid pK8-1, and the unique HindIII site of plasmid pBR322. The gene product encoded by this construction terminates at or about codon 565 and has a ~MW of 62,000 The activity of this gene product in a biological assay using tobacco budworm larvae is very low when compared to pΔ649. This plasmid can be recombined with a fragment derived from the construction described in Example 5 to regenerate a gene encoding a fully active protein toxin.

EXAMPLE 5

Preparation of Recombinant Plasmid pDW1.

Plasmid pDW1, which contains the essential domain of toxicity, can be prepared by digestion of plasmid pΔ649 with HindIII and standard electrophoresis gel isolation of a 285 bp fragment. This fragment can be cloned into the unique HindIII site of the multiple cloning site of any pUC plasmid, pUC8 ( Supplied by Pharmacia, Piscataway, N.J.) for example, to give plasmid pDW1. This vector can then be used as a vehicle to produce quantities of this 285 bp HindIII fragment. Excision of this fragment from pDW1 and cloning into the HindIII site of pKΔH results in the reconstruction of a gene which encodes an active δ-endotoxin in one out of two transformants. Selection can be done by standard antibody or toxicity screening.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C, or T if X is C
Y = A or G if X is T
W = C or A if Z is A or G
W = C if Z is C or T
Z = A, G, C or T if W is C
Z = A or G if W is A
QR = TC if S is A, G, C or T
J = A or G
K = T or C
L = A, T, C or G
M = A, C or T The above shows that the novel amino acid sequence of a protein can be prepared by equivalent nucleotide sequences encoding the same amino acid sequence of the proteins. Accordingly, the subject invention includes equivalent nucleotide sequences encoding the

*B.t.k.* δ-endotoxin of the subject invention. In addition it has been shown that proteins of identified structure and function may be constructed by changing the amino acid sequence if such changes do not alter the protein secondary or tertiary structure (Kaiser, E. T. and Kézdy, F. J. [1984] *Science* 223:249-255).

The work described herein was all done in conformity with physical and biological containment requirements specified in the NIH Guidelines.

CHART A

```
TTCATAAGAT GAGTCATATG GTTTAAATTG TAGTAATGAA AAACTGTATT ATATCATAAT

GAATTGGTAT CTTAATAAAA GAGATGGAGG TAACTT ATG GAT AAC AAT CCG AAC
                                         MET ASP ASN ASN PRO ASN
                                          1

ATC AAT GAA TGC ATT CCT TAT AAT TGT TTA AGT AAC CCT GAA GTA GAA
ILE ASN GLU CYS ILE PRO TYR ASN CYS LEU SER ASN PRO GLU VAL GLU
         10                                  20

GTA TTA GGT GGA GAA AGA ATA GAA ACT GGT TAC ACC CCA ATC GAT ATT
VAL LEU GLY GLY GLU ARG ILE GLU THR GLY TYR THR PRO ILE ASP ILE
        N70          N40 30

TCC TTG TCG CTA ACG CAA TTT CTT TTG AGT GAA TTT GTT CCC GGT GCT
SER LEU SER LEU THR GLN PHE LEU LEU SER GLU PHE VAL PRO GLY ALA
    40                                50

GGA TTT GTG TTA GGA CTA GTT GAT ATA ATA TGG GGA ATT TTT GGT CCC
GLY PHE VAL LEU GLY LEU VAL ASP ILE ILE TRP GLY ILE PHE GLY PRO
             60                                          70

TCT CAA TGG GAC GCA TTT CTT GTA CAA ATT GAA CAG TTA ATT AAC CAA
SER GLN TRP ASP ALA PHE LEU VAL GLN ILE GLU GLN LEU ILE ASN GLN
                                 80

AGA ATA GAA GAA TTC GCT AGG AAC CAA GCC ATT TCT AGA TTA GAA GGA
ARG ILE GLU GLU PHE ALA ARG ASN GLN ALA ILE SER ARG LEU GLU GLY
            90                                      100

CTA AGC AAT CTT TAT CAA ATT TAC GCA GAA TCT TTT AGA GAG TGG GAA
LEU SER ASN LEU TYR GLN ILE TYR ALA GLU SER PHE ARG GLU TRP GLU
                     110

GCA GAT CCT ACT AAT CCA GCA TTA AGA GAA GAG ATG CGT ATT CAA TTC
ALA ASP PRO THR ASN PRO ALA LEU ARG GLU GLU MET ARG ILE GLN PHE
120                                      130

AAT GAC ATG AAC AGT GCC CTT ACA ACC GCT ATT CCT CTT TTT GCA GTT
ASN ASP MET ASN SER ALA LEU THR THR ALA ILE PRO LEU PHE ALA VAL
                140                                      150

CAA AAT TAT CAA GTT CCT CTT TTA TCA GTA TAT GTT CAA GCT GCA AAT
GLN ASN TYR GLN VAL PRO LEU LEU SER VAL TYR VAL GLN ALA ALA ASN
                                 160

TTA CAT TTA TCA GTT TTG AGA GAT GTT TCA GTG TTT GGA CAA AGG TGG
LEU HIS LEU SER VAL LEU ARG ASP VAL SER VAL PHE GLY GLN ARG TRP
        170                                          180

GGA TTT GAT GCC GCG ACT ATC AAT AGT CGT TAT AAT GAT TTA ACT AGG
GLY PHE ASP ALA ALA THR ILE ASN SER ARG TYR ASN ASP LEU THR ARG
                         190

CTT ATT GGC AAC TAT ACA GAT CAT GCT GTA CGC TGG TAC AAT ACG GGA
LEU ILE GLY ASN TYR THR ASP HIS ALA VAL ARG TRP TYR ASN THR GLY
200                                      210

TTA GAG CGT GTA TGG GGA CCG GAT TCT AGA GAT TGG ATA AGA TAT AAT
LEU GLU ARG VAL TRP GLY PRO ASP SER ARG ASP TRP ILE ARG TYR ASN
                220                                          230

CAA TTT AGA AGA GAA TTA ACA CTA ACT GTA TTA GAT ATC GTT TCT CTA
GLN PHE ARG ARG GLU LEU THR LEU THR VAL LEU ASP ILE VAL SER LEU
                                 240

TTT CCC AAC TAT GAT AGT AGA ACG TAT CCA ATT CGA ACA GTT TCC CAA
PHE PRO ASN TYR ASP SER ARG THR TYR PRO ILE ARG THR VAL SER GLN
        250                                          260

TTA ACA AGA GAA ATT TAT ACA AAC CCA GTA TTA GAA AAT TTT GAT GGT
LEU THR ARG GLU ILE TYR THR ASN PRO VAL LEU GLU ASN PHE ASP GLY
                         270
```

-continued
CHART A

```
AGT TTT CGA GGC TCG GCT CAG GGC ATA GAA GGA AGT ATT AGG AGT CCA
SER PHE ARG GLY SER ALA GLN GLY ILE GLU GLY SER ILE ARG SER PRO
    280                             290

CAT TTG ATG GAT ATA CTT AAC AGT ATA ACC ATC TAT ACG GAT GCT CAT
HIS LEU MET ASP ILE LEU ASN SER ILE THR ILE TYR THR ASP ALA HIS
            300                                             310

AGA GGA GAA TAT TAT TGG TCA GGG CAT CAA ATA ATG GCT TCT CCT GTA
ARG GLY GLU TYR TYR TRP SER GLY HIS GLN ILE MET ALA SER PRO VAL
                                320

GGG TTT TCG GGG CCA GAA TTC ACT TTT CCG CTA TAT GGA ACT ATG GGA
GLY PHE SER GLY PRO GLU PHE THR PHE PRO LEU TYR GLY THR MET GLY
        330                                     340

AAT GCA GCT CCA CAA CAA CGT ATT GTT GCT CAA CTA GGT CAG GGC GTG
ASN ALA ALA PRO GLN GLN ARG ILE VAL ALA GLN LEU GLY GLN GLY VAL
                            350

TAT AGA ACA TTA TCG TCC ACT TTA TAT AGA AGA CCT TTT AAT ATA GGG
TYR ARG THR LEU SER SER THR LEU TYR ARG ARG PRO PHE ASN ILE GLY
    360                                 370

ATA AAT AAT CAA CAA CTA TCT GTT CTT GAC GGG ACA GAA TTT GCT TAT
ILE ASN ASN GLN GLN LEU SER VAL LEU ASP GLY THR GLU PHE ALA TYR
                    380                                     390

GGA ACC TCC TCA AAT TTG CCA TCC GCT GTA TAC AGA AAA AGC GGA ACG
GLY THR SER SER ASN LEU PRO SER ALA VAL TYR ARG LYS SER GLY THR
                                400

GTA GAT TCG CTG GAT GAA ATA CCG CCA CAG AAT AAC AAC GTG CCA CCT
VAL ASP SER LEU ASP GLU ILE PRO PRO GLN ASN ASN ASN VAL PRO PRO
        410                                         420

AGG CAA GGA TTT AGT CAT CGA TTA AGC CAT GTT TCA ATG TTT CGT TCA
ARG GLN GLY PHE SER HIS ARG LEU SER HIS VAL SER MET PHE ARG SER
                            430

GGC TTT AGT AAT AGT AGT GTA AGT ATA ATA AGA GCT CCT ATG TTC TCT
GLY PHE SER ASN SER SER VAL SER ILE ILE ARG ALA PRO MET PHE SER
    440                                 450

TGG ATA CAT CGT AGT GCT GAA TTT AAT AAT ATA ATT CCT TCA TCA CAA
TRP ILE HIS ARG SER ALA GLU PHE ASN ASN ILE ILE PRO SER SER GLN
                    460                                     470

ATT ACA CAA ATA CCT TTA ACA AAA TCT ACT AAT CTT GGC TCT GGA ACT
ILE THR GLN ILE PRO LEU THR LYS SER THR ASN LEU GLY SER GLY THR
                                480

TCT GTC GTT AAA GGA CCA GGA TTT ACA GGA GGA GAT ATT CTT CGA AGA
SER VAL VAL LYS GLY PRO GLY PHE THR GLY GLY ASP ILE LEU ARG ARG
        490                                         500

ACT TCA CCT GGC CAG ATT TCA ACC TTA AGA GTA AAT ATT ACT GCA CCA
THR SER PRO GLY GLN ILE SER THR LEU ARG VAL ASN ILE THR ALA PRO
                            510

TTA TCA CAA AGA TAT CGG GTA AGA ATT CGC TAC GCT TCT ACC ACA AAT
LEU SER GLN ARG TYR ARG VAL ARG ILE ARG TYR ALA SER THR THR ASN
    520                                 530

TTA CAA TTT CAT ACA TCA ATT GAC GGA AGA CCT ATT AAT CAG GGG AAT
LEU GLN PHE HIS THR SER ILE ASP GLY ARG PRO ILE ASN GLN GLY ASN
                    540                                     550

TTT TCA GCA ACT ATG AGT AGT GGG AGT AAT TTA CAG TCC GGA AGC TTT
PHE SER ALA THR MET SER SER GLY SER ASN LEU GLN SER GLY SER PHE
                                560

AGG ACT GTA GGT TTT ACT ACT CCG TTT AAC TTT TCA AAT GGA TCA AGT
ARG THR VAL GLY PHE THR THR PRO PHE ASN PHE SER ASN GLY SER SER
        570                                         580

GTA TTT ACG TTA AGT GCT CAT GTC TTC AAT TCA GGC AAT GAA GTT TAT
VAL PHE THR LEU SER ALA HIS VAL PHE ASN SER GLY ASN GLU VAL TYR
                            590
```

CHART A
-continued

```
ATA GAT CGA ATT GAA TTT GTT CCG GCA GAA
ILE ASP ARG ILE GLU PHE VAL PRO ALA GLU LYS HIS
600                                      610
```

CHART B

```
...  TTT AGG ACT GTA GGT TTT ACT ACT CCG TTT  AAC  TTT  TCA AAT GGA TCA  AGT  GTA  TTT ACG  TTA
     PHE ARG THR VAL GLY PHE THR THR PRO PHE  ASN  PHE  SER ASN GLY SER  SER  VAL  PHE THR  LEU
     570                                                580

AGT  GCT  CAT GTC  TTC  AAT  TCA GGC AAT GAA GTT TAT ATA GAT CGA ATT GAA TTT GTT CCG  GCA  GAA
SER  ALA  HIS VAL  PHE  ASN  SER GLY ASN GLU VAL TYR ILE ASP ARG ILE GLU PHE VAL PRO  ALA  GLU
          590                600
```

We claim:

1. A protein characterized by being a gene expression product insecticidally active against tobacco budworm larvae and by an amino acid sequence consisting of a total of 608 to 610 amino acids, in which sequence the amino acids from amino acid position number 1 extending through amino acid position number 608 are sequentially:

MET ASP ASN ASN PRO ASN ILE ASN GLU CYS ILE PRO TYR ASN CYS LEU SER ASN PRO GLU VAL GLU VAL LEU GLY GLY GLU ARG ILE GLU THR GLY TYR THR PRO ILE ASP ILE SER LEU SER LEU THR GLN PHE LEU LEU SER GLU PHE VAL PRO GLY ALA GLY PHE VAL LEU GLY LEU VAL ASP ILE ILE TRP GLY ILE PHE GLY PRO SER GLN TRP ASP ALA PHE LEU VAL GLN ILE GLU GLN LEU ILE ASN GLN ARG ILE GLU GLU PHE ALA ARG ASN GLN ALA ILE SER ARG LEU GLU GLY LEU SER ASN LEU TYR GLN ILE TYR ALA GLU SER PHE ARG GLU TRP GLU ALA ASP PRO THR ASN PRO ALA LEU ARG GLU GLU MET ARG ILE GLN PHE ASN ASP MET ASN SER ALA LEU THR THR ALA ILE PRO LEU PHE ALA VAL GLN ASN TYR GLN VAL PRO LEU LEU SER VAL TYR VAL GLN ALA ALA ASN LEU HIS LEU SER VAL LEU ARG ASP VAL SER VAL PHE GLY GLN ARG TRP GLY PHE ASP ALA ALA THR ILE ASN SER ARG TYR ASN ASP LEU THR ARG LEU ILE GLY ASN TYR THR ASP HIS ALA VAL ARG TRP TYR ASN THR GLY LEU GLU ARG VAL TRP GLY PRO ASP SER ARG ASP TRP ILE ARG TYR ASN GLN PHE ARG ARG GLU LEU THR LEU THR VAL LEU ASP ILE VAL SER LEU PHE PRO ASN TYR ASP SER ARG THR TYR PRO ILE ARG THR VAL SER GLN LEU THR ARG GLU ILE TYR THR ASN PRO VAL LEU GLU ASN PHE ASP GLY SER PHE ARG GLY SER ALA GLN GLY ILE GLU GLY SER ILE ARG SER PRO HIS LEU MET ASP ILE LEU ASN SER ILE THR ILE TYR THR ASP ALA HIS ARG GLY GLU TYR TYR TRP SER GLY HIS GLN ILE MET ALA SER PRO VAL GLY PHE SER GLY PRO GLU PHE THR PHE PRO LEU TYR GLY THR MET GLY ASN ALA ALA PRO GLN GLN ARG ILE VAL ALA GLN LEU GLY GLN GLY VAL TYR ARG THR LEU SER SER THR LEU TYR ARG ARG PRO PHE ASN ILE GLY ILE ASN ASN GLN GLN LEU SER VAL LEU ASP GLY THR GLU PHE ALA TYR GLY THR SER SER ASN LEU PRO SER ALA VAL TYR ARG LYS SER GLY THR VAL ASP SER LEU ASP GLU ILE PRO PRO GLN ASN ASN ASN VAL PRO PRO ARG GLN GLY PHE SER HIS ARG LEU SER HIS VAL SER MET PHE ARG SER GLY PHE SER ASN SER SER VAL SER ILE ILE ARG ALA PRO MET PHE SER TRP ILE HIS ARG SER ALA GLU PHE ASN ASN ILE ILE PRO SER SER GLN ILE THR GLN ILE PRO LEU THR LYS SER THR ASN LEU GLY SER GLY THR SER VAL VAL LYS GLY PRO GLY PHE THR GLY GLY ASP ILE LEU ARG ARG THR SER PRO GLY GLN ILE SER THR LEU ARG VAL ASN ILE THR ALA PRO LEU SER GLN ARG TYR ARG VAL ARG ILE ARG TYR ALA SER THR THR ASN LEU GLN PHE HIS THR SER ILE ASP GLY ARG PRO ILE ASN GLN GLY ASN PHE SER ALA THR MET SER SER GLY SER ASN LEU GLN SER GLY SER PHE ARG THR VAL GLY PHE THR THR PRO PHE ASN PHE SER ASN GLY SER SER VAL PHE THR LEU SER ALA HIS VAL PHE ASN SER GLY ASN GLU VAL TYR ILE ASP ARG ILE GLU PHE VAL PRO ALA GLU.

2. The protein gene expression product of claim 1 consisting of *Bacillus thuringiensis* kurstaki δ-endotoxin having the following 610 amino acid sequence:
MET ASP ASN ASN PRO ASN ILE ASN GLU CYS ILE PRO TYR ASN CYS LEU SER ASN PRO GLU VAL GLU VAL LEU GLY GLY GLU ARG ILE GLU THR GLY TYR THR PRO ILE ASP ILE SER LEU SER LEU THR GLN PHE LEU LEU SER GLU PHE VAL PRO GLY ALA GLY PHE VAL LEU GLY LEU VAL ASP ILE ILE TRP GLY ILE PHE GLY PRO SER GLN TRP ASP ALA PHE LEU VAL GLN ILE GLU GLN LEU ILE ASN GLN ARG ILE GLU GLU PHE ALA ARG ASN GLN ALA ILE SER ARG LEU GLU GLY LEU SER ASN LEU TYR GLN ILE TYR ALA GLU SER PHE ARG GLU TRP GLU ALA ASP PRO THR ASN PRO ALA LEU ARG GLU GLU MET ARG ILE GLN PHE ASN ASP MET ASN SER ALA LEU THR THR ALA ILE PRO LEU PHE ALA VAL GLN ASN TYR GLN VAL PRO LEU LEU SER VAL TYR VAL GLN ALA ALA ASN LEU HIS LEU SER VAL LEU ARG ASP VAL SER VAL PHE GLY GLN ARG TRP GLY PHE ASP ALA ALA THR ILE ASN SER ARG TYR ASN ASP LEU THR ARG LEU ILE GLY ASN TYR THR ASP HIS ALA VAL ARG TRP TYR ASN THR GLY LEU GLU ARG VAL TRP GLY PRO ASP SER ARG ASP TRP
ILE ARG TYR ASN GLN PHE ARG ARG GLU
LEU THR LEU THR VAL LEU ASP ILE VAL
SER LEU PHE PRO ASN TYR ASP SER ARG
THR TYR PRO ILE ARG THR VAL SER GLN
LEU THR ARG GLU ILE TYR THR ASN PRO
VAL LEU GLU ASN PHE ASP GLY SER PHE
ARG GLY SER ALA GLN GLY ILE GLU GLY
SER ILE ARG SER PRO HIS LEU MET ASP ILE
LEU ASN SER ILE THR ILE TYR THR ASP
ALA HIS ARG GLY GLU TYR TYR TRP SER
GLY HIS GLN ILE MET ALA SER PRO VAL
GLY PHE SER GLY PRO GLU PHE THR PHE
PRO LEU TYR GLY THR MET GLY ASN ALA
ALA PRO GLN GLN ARG ILE VAL ALA GLN
LEU GLY GLN GLY VAL TYR ARG THR LEU
SER SER THR LEU TYR ARG ARG PRO PHE
ASN ILE GLY ILE ASN ASN GLN GLN LEU
SER VAL LEU ASP GLY THR GLU PHE ALA
TYR GLY THR SER SER ASN LEU PRO SER
ALA VAL TYR ARG LYS SER GLY THR VAL
ASP SER LEU ASP GLU ILE PRO PRO GLN
ASN ASN ASN VAL PRO PRO ARG GLN GLY
PHE SER HIS ARG LEU SER HIS VAL SER
MET PHE ARG SER GLY PHE SER ASN SER
SER VAL SER ILE ILE ARG ALA PRO MET
PHE SER TRP ILE HIS ARG SER ALA GLU
PHE ASN ASN ILE ILE PRO SER SER GLN ILE
THR GLN ILE PRO LEU THR LYS SER THR
ASN LEU GLY SER GLY THR SER VAL VAL
LYS GLY PRO GLY PHE THR GLY GLY ASP
ILE LEU ARG ARG THR SER PRO GLY GLN
ILE SER THR LEU ARG VAL ASN ILE THR
ALA PRO LEU SER GLN ARG TYR ARG VAL
ARG ILE ARG TYR ALA SER THR THR ASN
LEU GLN PHE HIS THR SER ILE ASP GLY
ARG PRO ILE ASN GLN GLY ASN PHE SER
ALA THR MET SER SER GLY SER ASN LEU
GLN SER GLY SER PHE ARG THR VAL GLY
PHE THR THR PRO PHE ASN PHE SER ASN
GLY SER SER VAL PHE THR LEU SER ALA
HIS VAL PHE ASN SER GLY ASN GLU VAL
TYR ILE ASP ARG ILE GLU PHE VAL PRO
ALA GLU LYS HIS.

3. The protein gene expression product of claim 1 consisting of the following 610 amino acid sequence:
MET ASP ASN ASN PRO ASN ILE ASN GLU CYS
ILE PRO TYR ASN CYS LEU SER ASN PRO
GLU VAL GLU VAL LEU GLY GLY GLU ARG
ILE GLU THR GLY TYR THR PRO ILE ASP
ILE SER LEU SER LEU THR GLN PHE LEU
LEU SER GLU PHE VAL PRO GLY ALA GLY
PHE VAL LEU GLY LEU VAL ASP ILE ILE
TRP GLY ILE PHE GLY PRO SER GLN TRP
ASP ALA PHE LEU VAL GLN ILE GLU GLN
LEU ILE ASN GLN ARG ILE GLU GLU PHE
ALA ARG ASN GLN ALA ILE SER ARG LEU
GLU GLY LEU SER ASN LEU TYR GLN ILE
TYR ALA GLU SER PHE ARG GLU TRP GLU
ALA ASP PRO THR ASN PRO ALA LEU ARG
GLU GLU MET ARG ILE GLN PHE ASN ASP
MET ASN SER ALA LEU THR THR ALA ILE
PRO LEU PHE ALA VAL GLN ASN TYR GLN
VAL PRO LEU LEU SER VAL TYR VAL GLN ALA ALA ASN LEU HIS LEU SER VAL LEU
ARG ASP VAL SER VAL PHE GLY GLN ARG
TRP GLY PHE ASP ALA ALA THR ILE ASN
SER ARG TYR ASN ASP LEU THR ARG LEU
ILE GLY ASN TYR THR ASP HIS ALA VAL
ARG TRP TYR ASN THR GLY LEU GLU ARG
VAL TRP GLY PRO ASP SER ARG ASP TRP
ILE ARG TYR ASN GLN PHE ARG ARG GLU
LEU THR LEU THR VAL LEU ASP ILE VAL
SER LEU PHE PRO ASN TYR ASP SER ARG
THR TYR PRO ILE ARG THR VAL SER GLN
LEU THR ARG GLU ILE TYR THR ASN PRO
VAL LEU GLU ASN PHE ASP GLY SER PHE
ARG GLY SER ALA GLN GLY ILE GLU GLY
SER ILE ARG SER PRO HIS LEU MET ASP ILE
ILE ASN SER ILE THR ILE TYR THR ASP
ALA HIS ARG GLY GLU TYR TYR TRP SER
GLY HIS GLN ILE MET ALA SER PRO VAL
GLY PHE SER GLY PRO GLU PHE THR PHE
PRO LEU TYR GLY THR MET GLY ASN ALA
ALA PRO GLN GLN ARG ILE VAL ALA GLN
LEU GLY GLN GLY VAL TYR ARG THR LEU
SER SER THR LEU TYR ARG ARG PRO PHE
ASN ILE GLY ILE ASN ASN GLN GLN LEU
SER VAL LEU ASP GLY THR GLU PHE ALA
TYR GLY THR SER SER ASN LEU PRO SER
ALA VAL TYR ARG LYS SER GLY THR VAL
ASP SER LEU ASP GLU ILE PRO PRO GLN
ASN ASN ASN VAL PRO PRO ARG GLN GLY
PHE SER HIS ARG LEU SER HIS VAL SER
MET PHE ARG SER GLY PHE SER ASN SER
SER VAL SER ILE ILE ARG ALA PRO MET
PHE SER TRP ILE HIS ARG SER ALA GLU HE
ASN ASN ILE ILE PRO SER SER GLN ILE
THR GLN ILE PRO LEU THR LYS SER THR
ASN LEU GLY SER GLY THR SER VAL VAL
LYS GLY PRO GLY PHE THR GLY GLY ASP
ILE LEU ARG ARG THR SER PRO GLY GLN
ILE SER THR LEU ARG VAL ASN ILE THR
ALA PRO LEU SER GLN ARG TYR ARG VAL
ARG ILE ARG TYR ALA SER THR THR ASN
LEU GLN PHE HIS THR SER ILE ASP GLY
ARG PRO ILE ASN GLN GLY ASN PHE SER
ALA THR MET SER SER GLY SER ASN LEU
GLN SER GLY SER PHE ARG THR VAL GLY
PHE THR THR PRO PHE ASN PHE SER ASN
GLY SER SER VAL PHE THR LEU SER ALA
HIS VAL PHE ASN SER GLY ASN GLU VAL
TYR ILE ASP ARG ILE GLU PHE VAL PRO
ALA GLU VAL THR.

4. A protein characterized by being a gene expression product insecticidally active against tobacco budworm larvae and by an amino acid sequence consisting of a total of 608 to 610 amino acids, in which sequence the amino acids from amino acid position number 566 extending through amino acid position number 608 are sequentially:
PHE ARG THR VAL GLY PHE THR THR PRO
PHE ASN PHE SER ASN GLY SER SER VAL
PHE THR LEU SER ALA HIS VAL PHE ASN
SER GLY ASN GLU VAL TYR ILE ASP ARG
ILE GLU PHE VAL PRO ALA GLU.

* * * * *